United States Patent [19]

Dioguardi

[11] Patent Number: 5,074,873
[45] Date of Patent: Dec. 24, 1991

[54] DISPOSABLE TOURNIQUET

[76] Inventor: Francesco S. Dioguardi, Via Ciovasso, 11, 20121 Milano, Italy

[21] Appl. No.: 423,775

[22] Filed: Oct. 17, 1989

[30] Foreign Application Priority Data

Oct. 19, 1988 [IT] Italy .................... 22040/88[U]

[51] Int. Cl.⁵ .............................................. A61B 17/12
[52] U.S. Cl. ............................... 606/203; 139/387 R; 139/420 B; 87/9
[58] Field of Search ............... 606/203; 139/387 R, 139/420 B; 70/16; 446/26; 87/9

[56] References Cited

U.S. PATENT DOCUMENTS

| 869,686 | 10/1907 | Bauno | 446/26 |
|---|---|---|---|
| 1,268,932 | 6/1918 | Corrigan | 128/84 R |
| 1,376,618 | 5/1921 | Hansen | 139/387 R |
| 1,814,224 | 7/1931 | Murphy | 139/420 B |
| 2,117,974 | 5/1938 | Moore | 139/388 X |
| 2,783,758 | 3/1957 | Trott | 128/84 R |
| 3,130,630 | 4/1964 | Dawes | 87/9 X |
| 3,872,861 | 3/1975 | Tamny et al. | 128/84 R |
| 4,777,859 | 10/1988 | Plummer | 139/387 R X |

Primary Examiner—Michael H. Thaler

[57] ABSTRACT

A disposable tourniquet is disclosed which includes a tubular component consisting of a diagonally interwoven fibrous material fabric of vegetable, synthetic or mixed type and, when desired, of an elastic component.

3 Claims, 1 Drawing Sheet

DISPOSABLE TOURNIQUET

BACKGROUND OF THE INVENTION

1. Field of the Invention

This invention relates to a tourniquet consisting of a fibrous material structure with an elasticity equivalent to that of traditional rubber tourniquets but substantially cheaper to produce and therefore suitable for a single use.

The tourniquet, according to the present invention, shows highly useful characteristics, as will be shown in the following detailed description.

2. Description of Related Art

The spread of highly infectious viral diseases has accentuated the need for adequate preventive measures in regard to sanitary materials.

For example, disposable syringes are generally used by health services and by individuals instead of glass syringes.

This provides a maximum guarantee against infections along with maximum practicality. In fact, it is not economical to sterilize syringes, since sterilization costs more than the syringe itself.

Similar statements can be made for bandages, gauzes, tapes and bandaids, once recycled after sterilization and now thrown away after one use.

The decisive factor in this development was their manufacture out of paper, due in part to the mechanical strength (especially stretch resistance) of this material and to the ease of disposing of them by incineration without polluting the environment.

For these reasons, smocks, masks, hats, drapes and sheets in operating room are now made of disposable cellulose fibre materials.

In addition, much attention is now given to protecting the medical and paramedical personnel from accidental injection by infectious blood and there are continuous public campaigns not to use syringes previously used by others.

However, no attention has been paid to the tourniquet, which is indispensable to anyone who has to give an intravenous injection.

There are several kinds of tourniquets. The most widely used is the traditional rubber tube used for many patients in succession and over long periods of time.

Since the appearance of the acquired immuno-deficiency syndrome (AIDS), a great deal of attention has been paid to the risks of transmission of the infection from patient to patient or from patient to persons treating him, or vice versa.

Therefore, it would be helpful to have a disposable tourniquet available to avoid even the possibility of being contaminated.

SUMMARY OF THE INVENTION

This object has been achieved with the tourniquet according to the invention, which consists of a tube made of a diagonally woven fibrous mesh, and, if desired, containing an elastic component.

These and other characteristics and advantages of the tourniquet, according to the present invention, will be made more evident by the following description illustrated by the enclosed figures.

BRIEF DESCRIPTION OF THE DRAWINGS

FIG. 1 with no elastic component, FIG. 2 with peripheral elastic system and FIG. 4 with a central elastic system.

DETAILED DESCRIPTION OF PREFERRED EMBODIMENTS

Figure 1:
FIGS. 1, 2 and 4 indicate three ways to prepare the tourniquet.

Referring to the reference numerals in the various figures: 1 is the fibre material fabric which can be vegetable, synthetic or mixed.

This fabric is woven diagonally and can consist for example of interwoven threads or tapes.

Figure 2:
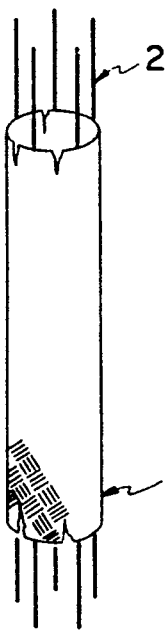
Figure 3:
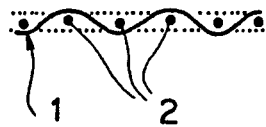
FIG. 3 shows a transverse section of the tourniquet of FIG. 2.

Preferably the fibrous material is cellulose paper. An elastic component 2 as in FIG. 2, consists of multiple elastic fibres inserted into the mesh of the fibrous component.

Figure 4:
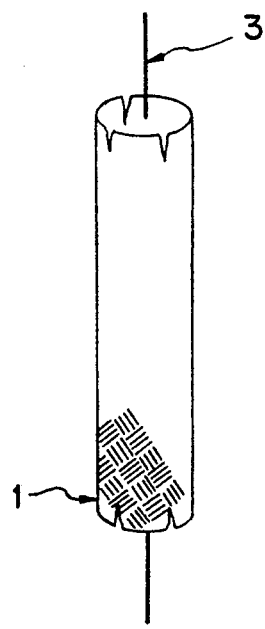

An elastic component 3 consisting of an elastic system is inserted in a central position with respect to the tubular component as shown in FIG. 4.

The described tubular structure, with or without elastic filaments, provides the tourniquet, according to this invention, with adequate elasticity, equal to that of rubber tourniquets.

Figure 5:
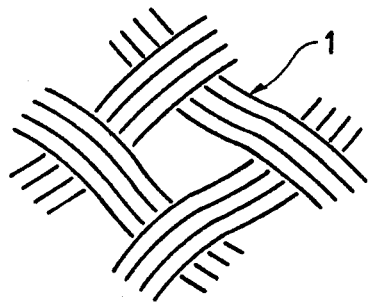
FIGS. 5 and 6 are two different embodiments of the tubular fabric component and FIG. 7 shows the application of the tourniquet to the arm.
Figure 6:
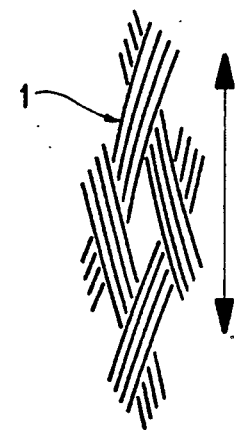
Figure 7:
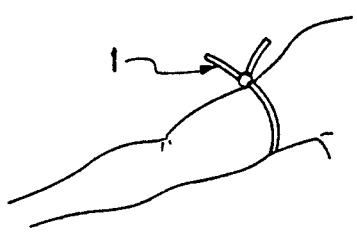

The behavior of the tubular structure when stretched is illustrated by the comparison between the situation in FIG. 5 (unstretched condition) and FIG. 6 (stretched condition).

The structure in a stretched condition allows a considerable elongation of the tourniquet. The structure allows in any case a return to the starting dimension, due also to the elastic filaments provided therein.

Obviously, the ends of the tourniquet are sealed or treated in such a way to avoid unravelling.

From the above description it is evident how the invention brings about the desired results.

In detail, it provides a tourniquet of little cost to be employed for a single use, with the additional advantage that it can be destroyed by incineration without polluting the atmosphere.

I claim:

1. A disposable tourniquet comprising:
   a diagonally interwoven fibrous material in the shape of a continuous tubular construction and being stretchable in a longitudinal direction; and
   at least one elastic component integrally provided in connection with said interwoven fibrous material in a longitudinal direction thereof, wherein said fibrous material consists of paper and an elasticity of said disposable tourniquet is equivalent to a rubber tourniquet.

2. The disposable tourniquet according to claim 1, wherein said at least one elastic component is a plurality of elastic filaments inserted into a mesh of the fibrous component.

3. The disposable tourniquet according to claim 1, wherein said at least one elastic component consists of an elastic system inserted in a longitudinally central position with respect to the tubular component.

* * * * *